United States Patent
Vedage et al.

(10) Patent No.: US 11,505,643 B2
(45) Date of Patent: Nov. 22, 2022

(54) BENZYLATED TRIAMINONONANE AND USES THEREOF

(71) Applicants: Evonik Operations GmbH, Essen (DE); Gamini Ananda Vedage, Bethlehem, PA (US); Michael Cook, Macungie, PA (US); Sudhir Ananthachar, Hillsborough, NJ (US); Jamie Schneck, Allentown, PA (US)

(72) Inventors: Gamini Ananda Vedage, Bethlehem, PA (US); Michael Cook, Macungie, PA (US); Sudhir Ananthachar, Hillsborough, NJ (US); Jamie Schneck, Allentown, PA (US)

(73) Assignee: Evonik Operations GmbH, Essen (DE)

( * ) Notice: Subject to any disclaimer, the term of this patent is extended or adjusted under 35 U.S.C. 154(b) by 182 days.

(21) Appl. No.: 16/761,950

(22) PCT Filed: Nov. 9, 2017

(86) PCT No.: PCT/US2017/060759
§ 371 (c)(1),
(2) Date: May 6, 2020

(87) PCT Pub. No.: WO2019/094013
PCT Pub. Date: May 16, 2019

(65) Prior Publication Data
US 2021/0179769 A1    Jun. 17, 2021

(51) Int. Cl.
*C08G 59/50* (2006.01)
*C07C 209/68* (2006.01)
*C07C 211/49* (2006.01)

(52) U.S. Cl.
CPC ........ *C08G 59/5033* (2013.01); *C07C 209/68* (2013.01); *C07C 211/49* (2013.01)

(58) Field of Classification Search
None
See application file for complete search history.

(56) References Cited

U.S. PATENT DOCUMENTS

| | | |
|---|---|---|
| 6,262,148 B1 | 7/2001 | Cheng et al. |
| 8,147,964 B2 | 4/2012 | Vedage et al. |
| 8,168,296 B2 | 5/2012 | Vedage et al. |
| 8,318,309 B2 | 11/2012 | Vedage et al. |
| 8,729,213 B2 | 5/2014 | Raymond et al. |
| 9,340,682 B2 | 5/2016 | Burckhardt et al. |
| 2007/0276058 A1 | 11/2007 | Burckhardt et al. |
| 2009/0023846 A1 | 1/2009 | Vedage et al. |
| 2009/0030125 A1 | 1/2009 | Vedage et al. |
| 2009/0163676 A1 | 6/2009 | Vedage et al. |
| 2013/0079435 A1 | 3/2013 | Raymond et al. |
| 2014/0179829 A1 | 6/2014 | Burckhardt et al. |
| 2017/0218114 A1 * | 8/2017 | Kasemi ................. C07C 211/27 |

FOREIGN PATENT DOCUMENTS

| | | |
|---|---|---|
| CN | 1608089 A | 4/2005 |
| CN | 103562328 A | 2/2014 |
| CN | 103814057 A | 5/2014 |
| CN | 106715515 A | 5/2017 |
| CN | 107663268 A | 2/2018 |
| EP | 2108668 A1 | 10/2009 |
| GB | 1529740 A | 10/1978 |
| WO | 0001659 A1 | 1/2000 |
| WO | 2009080209 A1 | 7/2009 |
| WO | 2014067096 A1 | 5/2014 |
| WO | 2015085461 A1 | 6/2015 |

OTHER PUBLICATIONS

PCT International Search Report dated Mar. 13, 2018 corresponding to PCT Application No. PCT/US2017/060759 filed Nov. 9, 2017 (6 pages).
Office Action of Chinese Application No. 201780097934.3 dated Aug. 30, 2022.

\* cited by examiner

*Primary Examiner* — Megan McCulley
(74) *Attorney, Agent, or Firm* — Andrew H. Chung; Linda S. Li; Jason S. Ngui

(57) ABSTRACT

The present invention provides benzylated triaminononane compounds, epoxy curing agent compositions comprising benzylated triaminononane compounds and methods of making such compositions. Amine-epoxy compositions and articles produced from these amine-epoxy compositions are also disclosed.

20 Claims, No Drawings

BENZYLATED TRIAMINONONANE AND USES THEREOF

This Application is a § 371 national stage of PCT International Application No. PCT/US2017/060759, filed Nov. 9, 2017, the contents of which are hereby incorporated by reference in its entirety into this application.

BACKGROUND OF THE INVENTION

The present invention relates generally to benzylated triaminononane compounds, curing agent and amine-epoxy compositions derived from such compounds, and articles produced from such compounds and/or compositions.

The uses of epoxy resins which are cured, hardened, and/or crosslinked with amine-based curing agents are well known. These amine-epoxy materials are widely used in applications ranging from coatings, adhesives, and composites, to construction products for concrete, cementitious or ceramic substrates, often referred to as civil engineering applications such as formulations for concrete flooring.

Various methods have been used to reduce the carbamation in epoxy processing by reducing the amount of primary amines. One method includes adducting amines with mono or di glycidyl ethers. However, this method has the disadvantage of increasing the viscosity of the product. An additional method includes making a Michael addition of acrylonitrile on the primary amine. In that case the viscosity remains low but a retro reaction occurring, in time, releases free acrylonitrile, which makes the product highly toxic and difficult to handle.

When epoxy resins are cured with most non-aromatic amines, the miscibility of these amines with the epoxy resins is not always good and some incomplete cure can take place. This imperfect cure results in a whitening or greasy layer on the surface (blushing) and poor physical properties of the cured epoxy system. To improve the cure, diluents such as benzyl alcohol can be used. This introduces a potential VOC (volatile organic content) plasticizer into the epoxy system. Such systems once fully cured, will over a period of time, slowly emit these types of plasticizers into the atmosphere. Due to the introduction of more stringent environmental regulations, and a desire for many industries to meet new "green label" or "emission compliance" standards, there is a need for new products that can be used in both the industrial flooring and protective coating sectors that not only provide excellent cure properties, but also comply with regional emission directives. Examples of improved emission standards include AgBB, DIBt, Der Blaue Engel, Calif. CDPH and the US green building council (LEED).

Benzylation of amines was developed and used to overcome the issues with better through cure without any addition of solvents and plasticizers leading to new, emission compliant technology. The benzylation improved through cure compared to the basic amines. While it gave emission compliance systems, it also slowed down the reaction between the epoxy resin and the amine curing agent thus increasing the cure time.

U.S. Pat. No. 8,318,309, which is hereby incorporated by reference, discloses a curing agent for epoxy resin that is produced by benzylation of aminopropylated alkylenediamines. U.S. Pat. No. 8,168,296, which is hereby incorporated by reference, discloses a curing agent for epoxy resin that is produced by benzylation of polyalkylene polyamines. The reactions and products formed in U.S. Pat. Nos. 8,318,309 and 8,168,296 result in a wide range of products and properties, where it is desirable in the art to have greater tailorability and specific product specifications in the resultant benzylated products.

U.S. patent application publication number 2013/0079435 A1, which is hereby incorporated by reference, discloses a curing agent for epoxy resin that is produced by benzylation of metaxylylenediamine. The curing agents of U.S. patent application publication number 2013/0079435 A1 suffer from the drawback that the epoxy resin is very slow to cure.

There are numerous amine-based curing agents and amine-epoxy compositions that are employed in the amine-epoxy coating industry; however, known products fail to completely address the needs or solve the problems noted above. It has been important to find a benzylated amine that improves through cure but retains other properties such as cure speed and appearance at low temperature. Accordingly, it is to this end that the present invention is directed.

BRIEF SUMMARY OF THE INVENTION

The present invention discloses benzylated triaminononane compounds, curing agent compositions and methods of making such compositions. These curing agent compositions can be used to cure, harden, and/or crosslink an epoxy resin. The present invention comprises curing agent compositions comprising at least one benzylated triaminononane compound having at least three active amine hydrogen atoms and at least one benzyl group, which in one embodiment comprises the reaction product of the reductive amination of a benzaldehyde compound with a triaminononane (TAN) compound (Hexatran™, Ascend Performance Materials). In another embodiment the at least one benzylated TAN comprises the reaction product of a benzyl halide with a TAN.

In another exemplary embodiment, the present disclosure includes a method for forming a curing agent composition. The method includes contacting a benzaldehyde compound or benzyl halide with a triaminononane (TAN) compound. The benzaldehyde compound or benzyl halide compound is reacted with triaminononane under conditions sufficient to form a benzylated triaminononane compound.

In another exemplary embodiment, the present disclosure includes an amine-epoxy composition. The amine-epoxy composition includes the contact product of a curing agent composition including at least one benzylated triaminononane compound, the benzylated triaminononane compound being a reaction product of a benzaldehyde compound or benzyl halide compound and a triaminononane compound; and an epoxy composition comprising at least one multifunctional epoxy resin.

Amine-epoxy compositions using benzylated triaminononane compounds offer advantages in cure speed, carbamation resistance and water spotting, over amine-epoxy compositions using benzylated aminopropylated alkylenediamine compounds or benzylated metaxylylenediamine compounds.

In another exemplary embodiment, the present disclosure includes benzylated triaminononane compounds.

Other features and advantages of the present invention will be apparent from the following more detailed description of the preferred embodiment.

DETAILED DESCRIPTION OF THE INVENTION

Embodiments of the present disclosure include benzylated triaminononane compounds, curing agent compositions and methods of making such compositions. These curing agent compositions can be used to cure, harden, and/or crosslink an epoxy resin. One embodiment includes curing agent compositions comprising at least one benzylated triaminononane compound, the benzylated triaminononane compound being a reaction product of a benzaldehyde compound or benzyl halide compound and a triaminononane (TAN) compound. Generally, curing agent compositions, according to embodiments of the present disclosure, have an amine hydrogen equivalent weight (AHEW) based on 100% solids from about 50 to about 250, preferably 50 to about 150. The degree of benzylation depends on the equivalents ratio of benzaldehyde compound or benzyl halide compound to reactive amine hydrogens in the triaminononane compound, for example, in the reductive amination reaction. Thus, in an exemplary embodiment of the present disclosure, the curing agent composition comprises a benzylated triaminononane comprising one, or two, or three, or four, or five, or six benzyl groups, or any combination thereof.

In one aspect of this invention, the at least one benzylated triaminononane compound has the formula:

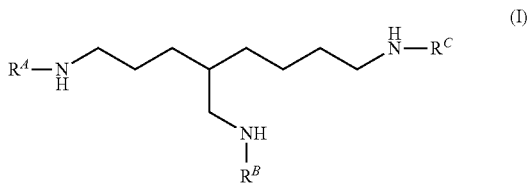

where $R^A$ is a substituted or unsubstituted benzyl group; $R^B$ and $R^C$ are independently $R^A$ or a hydrogen atom.

In another aspect of this invention, the at least one benzylated triaminononane compound has the formula:

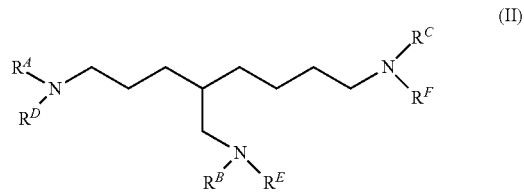

where $R^A$ is a substituted or unsubstituted benzyl group; $R^B$, $R^C$, $R^D$, $R^E$, and $R^F$ are independently $R^A$ or a hydrogen atom.

Given the many possible locations on the triaminononane compound where the benzyl groups can replace a hydrogen atom, the product resulting from the reductive reaction of at least one triaminononane compound and a benzaldehyde compound or from reaction with a benzyl halide is necessarily a mixture of many different species. In the benzylated TAN of formula (I), some of the $R^B$ and $R^C$ are hydrogen and others are benzyl groups. In the benzylated TAN of formula (II), some of the $R^B$, $R^C$, $R^D$, $R^E$, and $R^F$ are hydrogen and others are benzyl groups. Triaminononane is an amine having three primary amine groups. Benzylation of triaminononane produces tri-functional benzylated amine. Which and how many of the active amine hydrogens are converted to benzyl groups depends on many factors, among those being the reaction conditions, catalyst selection, reactants ratio, choice of reactant (benzaldehyde compound or specific halide compound), and the like. For example, using a benzaldehyde compound as the reactant in a molar reactant ratio of benzaldehyde to the triaminononane compound of about 1.2:1 produces about 40-50% mono-benzylated amines, about 30-40% di-benzylated amines, and about 1-5% tri-benzylated amines.

In another example, using a benzaldehyde compound as the reactant in a molar reactant ratio of benzaldehyde to the triaminononane compound of about 2:1 produces about 10-20% mono-benzylated amines, about 60-70% di-benzylated amines, and about 15-20% tri-benzylated amines.

In another example, using a benzaldehyde compound as the reactant in a molar reactant ratio of benzaldehyde to the triaminononane compound of about 3:1 produces about 0-2% mono-benzylated amines, about 1-4% di-benzylated amines, and about 90-98% tri-benzylated amines of triaminononane.

In another example, using a benzyl halide compound as the reactant in a molar reactant ratio of benzyl halide to the triaminononane compound of about 1.2:1 produces about 40-50% mono-benzylated amines, about 30-40% di-benzylated amines, and about 1-5% tri-benzylated amines.

In another example, using a benzyl halide compound as the reactant in a molar reactant ratio of benzyl halide to the triaminononane compound of about 2:1 produces about 10-20% mono-benzylated amines, about 60-70% di-benzylated amines, and about 15-20% tri-benzylated amines.

In another example, using a benzyl halide compound as the reactant in a molar reactant ratio of benzyl halide to the triaminononane compound of about 3:1 produces about 0-2% mono-benzylated amines, about 1-4% di-benzylated amines, and about 90-98% tri-benzylated amines of triaminononane.

The method for forming the benzylated triaminononane compound includes addition of a triaminononane compound and benzaldehyde followed by a reduction with $H_2$ in presence of a catalyst, such as a Pd/C catalyst. The benzylated triaminononane compound of formula (I) of the present invention can be prepared by the reductive amination of triaminononane with the benzaldehyde compound. Procedures for the reductive amination of benzaldehyde are generally known to those of skill in the art. Generally, these procedures involve condensing the benzaldehyde with the amine, then reducing the intermediate Schiff base. The reduction is typically conducted in the presence of a metal catalyst in a hydrogen-rich atmosphere at pressures above atmospheric pressure.

In accordance with the curing agent compositions and methods of making such compositions disclosed herein, the molar reactant ratio of the benzaldehyde compound to the at least one triaminononane compound is in a range from about 0.8:1 to about 3:1. In a preferred embodiment, the molar reactant ratio of the benzaldehyde compound to the at least one triaminononane compound is about 1.2:1 to about 2:1.

The benzylated triaminononane of formula (I) or formula (II) of the present disclosure can also be prepared by the reaction of at least one triaminononane compound with a benzyl halide. Generally, molar reactant ratios of the at least one benzyl halide compound to the at least one triaminononane compound are within a range from about 0.8:1 to about 3:1. In another aspect, the molar reactant ratio of the at least one benzyl halide to the at least one triaminononane compound is in a range from about 1.2:1 to about 2:1.

In another embodiment of this aspect of the present disclosure, the curing agent composition comprises a benzylated triaminononane of formula (I) component comprising triaminononane molecules having one, or two, or three benzyl groups, or any combination thereof. In one aspect, such benzylated triaminononane of formula (I) component for the present invention comprise at least 30 wt % triaminononane of formula (I) having at least two benzyl groups, i.e. having two or more benzyl groups. In other aspects, the benzylated triaminononane of formula (I) component comprise 20 to 90 wt %, especially 30 to 80 wt %, benzylated triaminononane of formula (I) having at least two benzyl groups. The curing agent composition, in this aspect of the present invention, can have an AHEW based on 100% solids from about 50 to about 250. Further, such curing agent composition can have an AHEW based on 100% solids in the range from about 50 to about 150. In these aspects, the preferred embodiment comprises benzylated triaminononane of formula (I).

In another embodiment of the present disclosure, the curing agent composition comprises a benzylated triaminononane of formula (II) component comprising triaminononane molecules having one, or two, or three, or four, or five, or six benzyl groups, or any combination thereof.

Other embodiments of the present disclosure include amine-epoxy compositions. For example, an amine-epoxy composition, in accordance with the present disclosure, includes the reaction product of A) at least one benzylated triaminononane compound; and B) an epoxy composition comprising at least one multifunctional epoxy resin. Optionally, various additives can be present in the compositions or formulations used to produce fabricated articles, dependent upon the desired properties. These additives can include, but are not limited to, solvents (including water), accelerators, plasticizers, fillers, fibers such as glass or carbon fibers, pigments, pigment dispersing agents, rheology modifiers, thixotropes, flow or leveling aids, surfactants, defoamers, biocides, or any combination thereof.

Benzaldehyde compounds suitable for use in the benzylation of the triaminononane compound include unsubstituted benzaldehyde and substituted benzaldehydes. Suitable substituted benzaldehydes include, but are not limited to, compounds of the formula PhCHO, where Ph is a moiety including an aromatic ring, in which Ph is unsubstituted or substituted with one or more of halogen atoms, $C_1$-$C_4$ alkyl, methoxy, ethoxy, amino, hydroxyl or cyano groups. In one embodiment, the benzaldehyde compound is benzaldehyde and in another embodiment, the benzaldehyde compound is vanillin.

Benzyl halide compounds suitable for use in the benzylation of the triaminononane include benzyl fluoride, benzyl chloride, benzyl bromide or benzyl iodide. The benzyl group may comprise unsubstituted benzyl or a substituted benzyl group. Substituted benzyl groups include, but are not limited to, radicals of the formula PhCH$_2$—, where Ph is a moiety including an aromatic ring, in which Ph is unsubstituted or substituted with one or more of halogen atoms, $C_1$-$C_4$ alkyl, methoxy, ethoxy, amino, hydroxyl or cyano groups. In one embodiment, the benzyl group is benzyl and in another embodiment the benzyl is vanillyl.

When the triaminononane compound is benzylated, the resultant product has a lower viscosity which allows benzylation to a point where there is little or no free TAN amine present in the final product. While not wishing to be bound by theory, it is believed that the removal of the free amine helps in reducing the carbamation of the film caused by the reaction of the primary amine in the presence of water and carbon dioxide. The decrease/absence of smoking or fuming; the improved compatibility with epoxy resin; the lower tendency to carbamate; and the low level of free, unreacted amine in the final product result in improved handling properties.

The AHEW for the benzylated triaminononane compound, AHEW, is determined using the following formula, assuming the benzylated triaminononane compound is the reductive amination product of x moles of benzaldehyde, for example, with 1 mole of triaminononane compound, Form1 (the triaminononane compound and the benzaldehyde are discussed in greater detail below):

$$AHEW = \frac{MW_{TAN} + x \cdot (MW_{Ald} - 16)}{f - x};$$

wherein:
$MW_{TAN}$ is the molecular weight of the triaminononane compound;
$MW_{Ald}$ is the molecular weight of the benzaldehyde;
f is the average amine hydrogen functionality of the triaminononane compound; and
x is the number of moles benzaldehyde used.

Amine-epoxy compositions of the present invention comprise the reaction product of a curing agent composition and an epoxy composition comprising at least one multifunctional epoxy resin. Multifunctional epoxy resin, as used herein, describes compounds containing 2 or more 1,2-epoxy groups per molecule. Epoxide compounds of this type are well known to those of skill in the art and are described in Y. Tanaka, "Synthesis and Characteristics of Epoxides", in C. A. May, ed., Epoxy Resins Chemistry and Technology (Marcel Dekker, 1988), which is incorporated herein by reference in its entirety.

The relative amount chosen for the epoxy composition versus that of the curing agent composition, or hardener, can vary depending upon, for example, the end-use article, its desired properties, and the fabrication method and conditions used to produce the end-use article. For instance, in coating applications using certain amine-epoxy compositions, incorporating more epoxy resin relative to the amount of the curing agent composition, can result in coatings which have increased drying time, but with increased hardness and improved appearance as measured by gloss. Amine-epoxy compositions of the present invention generally have stoichiometric ratios of epoxy groups in the epoxy composition to amine hydrogens in the curing agent composition ranging from about 1.5:1 to about 0.5:1. For example, such amine-epoxy compositions can have stoichiometric ratios of about 1.5:1, about 1.4:1, about 1.3:1, about 1.2:1, about 1.1:1, about 1:1, about 0.9:1, about 0.8:1, about 0.7:1, about 0.6:1 or about 0.5:1. In another aspect, the stoichiometric ratio ranges from about 1.3:1 to about 0.7:1. In yet another aspect, the stoichiometric ratio ranges from about 1.2:1 to about 0.8:1. In still another aspect, the stoichiometric ratio ranges from about 1.1:1 to about 0.9:1.

One class of epoxy resins suitable for use in the present invention comprises the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl)propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present invention:

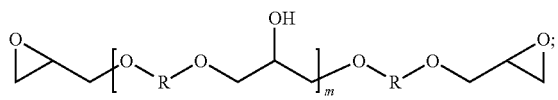

where m is an integer, and R is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of dihydric phenol. While in any given molecule the value of m is an integer, the materials are invariably mixtures which can be characterized by an average value of m, which is not necessarily a whole number. Polymeric materials with an average value of m between 0 and about 7 can be used in one aspect of the present invention.

In another aspect, epoxy novolac resins, which are the glycidyl ethers of novolac resins, can be used as multifunctional epoxy resins in accordance with the present invention. In yet another aspect, the at least one multifunctional epoxy resin is a diglycidyl ether of bisphenol-A (DGEBA), an advanced or higher molecular weight version of DGEBA, a diglycidyl ether of bisphenol-F, an epoxy novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from about 450 to 3000 or more. Because these products are solid at room temperature, they are often referred to as solid epoxy resins.

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature. Generally, multifunctional resins with EEW's based on solids of about 160 to about 750 are useful in the prevent invention. In another aspect the multifunctional epoxy resin has an EEW in a range from about 170 to about 250.

Depending upon the end-use application, it can be beneficial to reduce the viscosity of the compositions of the present invention by modifying the epoxy component. For example, the viscosity can be reduced to allow an increase in the level of pigment in a formulation or composition while still permitting easy application, or to allow the use of a higher molecular weight epoxy resin. Thus, it is within the scope of the present invention for the epoxy component, which comprises at least one multifunctional epoxy resin, to further comprise a monofunctional epoxide. Examples of monoepoxides include, but are not limited to, styrene oxide, cyclohexene oxide, ethylene oxide, propylene oxide, butylene oxide, and the glycidyl ethers of phenol, cresols, tert-butylphenol, other alkyl phenols, butanol, 2-ethylhexanol, $C_4$ to $C_{14}$ alcohols, and the like, or combinations thereof. The multifunctional epoxy resin can also be present in a solution or emulsion, with the diluent being water, an organic solvent, or a mixture thereof.

Compositions of the present invention can be used to produce various articles of manufacture. Depending on the requirements during the manufacturing of or for the end-use application of the article, various additives can be employed in the formulations and compositions to tailor specific properties. These additives include, but are not limited to, solvents (including water), accelerators, plasticizers, fillers, fibers such as glass or carbon fibers, pigments, pigment dispersing agents, rheology modifiers, thixotropes, flow or leveling aids, surfactants, defoamers, biocides, or any combination thereof. It is understood that other mixtures or materials that are known in the art can be included in the compositions or formulations and are within the scope of the present invention.

The present disclosure also is directed to articles of manufacture comprising the compositions disclosed herein. For example, an article can comprise an amine-epoxy composition which comprises the reaction product of a curing agent composition and an epoxy composition. Articles of manufacture produced from amine-epoxy compositions disclosed herein include, but are not limited to, adhesives, coatings, primers, sealants, curing compounds, construction products, flooring products, and composite products. Further, such coatings, primers, sealants, or curing compounds can be applied to metal or cementitious substrates. Coatings based on these amine-epoxy compositions can be solvent-free or can contain diluents, such as water or organic solvents, as needed for the particular application.

Coatings can contain various types and levels of pigments for use in paint and primer applications. Amine-epoxy coating compositions comprise a layer having a thickness ranging from 40 to 400 μm (micrometer), preferably 80 to 300 μm, more preferably 100 to 250 μm, for use in a protective coating applied on to metal substrates. In addition, for use in a flooring product or a construction product, coating compositions comprise a layer having a thickness ranging from 50 to 10,000 μm, depending on the type of product and the required end-properties. A coating product that delivers limited mechanical and chemical resistances comprises a layer having a thickness ranging from 50 to 500 μm, preferably 100 to 300 μm; whereas a coating product such as, for example, a self-leveling floor that delivers high mechanical and chemical resistances comprises a layer having a thickness ranging from 1,000 to 10,000 μm, preferably 1,500 to 5,000 μm.

Numerous substrates are suitable for the application of coatings of this invention with proper surface preparation, as is well known to one of ordinary skill in the art. Such substrates include, but are not limited to, concrete and various types of metals and alloys, such as steel and aluminum. Coatings of the present invention are suitable for the painting or coating of large metal objects or cementitious substrates including ships, bridges, industrial plants and equipment, and floors.

Coatings of this invention can be applied by any number of techniques including spray, brush, roller, paint mitt, and the like. In order to apply very high solids content or 100% solids coatings of this invention, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Construction and flooring applications include compositions comprising the amine-epoxy compositions of the present invention in combination with concrete or other materials commonly used in the construction industry. Applications of compositions of the present invention include, but are not limited to the composition's use as a primer, a deep penetrating primer, a coating, a curing compound, and/or a sealant for new or old concrete, such as referenced in ASTM C309-97, which is incorporated herein by reference. As a primer or a sealant, the amine-epoxy compositions of the present invention can be applied to surfaces to improve adhesive bonding prior to the application of a coating. As it pertains to concrete and cementitious application, a coating is an agent used for application on a surface to create a protective or decorative layer or a coat. Crack injection and crack filling products also can be prepared from the compositions disclosed herein. Amine-epoxy compositions of the present invention can be mixed with cementitious materials such as concrete mix to form polymer or modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

In a particular use of the invention, these curing agent compositions will have applicability in making epoxy filament-wound tanks, infusion composites such as windmill blades, aerospace adhesives, industrial adhesives, as well as other related applications. A composite is a material made of different substances, and in the case of resin technologies, composites refer to resin impregnated systems where the resin is reinforced by the addition of reinforcing materials such as fillers and fibers for improving general properties of the resulting product. These materials work together but are not soluble in one another. In the present case, the binder component comprises the epoxy resin and epoxy curing agent(s). There are many types of composite applications such as prepegs, laminates, filament windings, braiding, pultrusion, wet lay and infusion composites. Resin infusion, or resin transfer, is a process by which resin is introduced to the composite mold, the reinforcement material having already been placed into the mold and closed prior to resin introduction. There are variations on this process such as those that are vacuum assisted.

An advantage of the use of benzylated triaminononane compounds in amine-epoxy compositions for making composites is the longer pot life and improved compatibility versus the unmodified polyamines. The advantage in adhesives is again longer pot life, in this case, so there is no skin-over before the parts are glued together, which is a major concern for large aircraft and windmill blades, when it takes a long time to place the adhesive beads across the entire part. Lower blush due to the benzyl group adds to the lower skin-over. The low viscosity allows for high filler levels. If the adhesive that is put on the part first starts to cure or starts to blush over before the last of the adhesive is dispensed on the part, when the two pieces are pressed together, there will be a weaker bond with the first bead.

After heat cure, the benzylated curing agents of the invention show good physical properties, comparable to amines like isophoronediamine (IPDA), which are used in composites for mechanical strength and compatibility with epoxy resin (see table below). However, these benzylated triaminononane of formula (I) curing agents have a lower Tg compared to IPDA so they do not need as extensive a cure time/temperature in order to fully cure, resulting in lower processing and energy costs.

The present invention is directed to a benzylated triaminononane compound comprising the reaction product of a benzaldehyde compound or benzyl halide compound and a triaminononane compound. Preferably, the benzaldehyde compound is a substituted or unsubstituted benzaldehyde. Preferred benzyl halide compounds are benzyl fluoride, benzyl chloride, benzyl bromide and benzyl iodide. Preferably, the triaminononane compound is triaminononane. Preferably, the benzylated triaminononane compound is a benzylated triaminononane. Preferably, the benzylated triaminononane compound is a benzylated triaminononane of formula

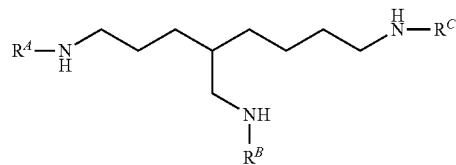

where $R^A$ is a substituted or unsubstituted benzyl group; $R^B$ and $R^C$ are independently $R^A$ or a hydrogen atom.

The present invention is also directed to a curing agent composition comprising at least one benzylated triaminononane compound, wherein the benzylated triaminononane compound comprises the reaction product of a benzaldehyde compound or benzyl halide compound and a triaminononane compound.

Preferably, the benzylated triaminononane compound has the following formula:

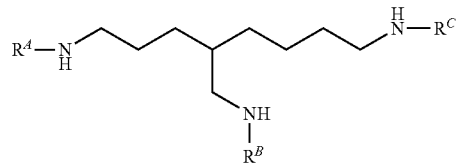

where $R^A$ is a substituted or unsubstituted benzyl group; $R^B$ and $R^C$ are independently $R^A$ or a hydrogen atom.

Preferably, the composition comprises about 10-20% mono-benzylated amines, about 60-70% di-benzylated amines, and about 15-20% tri-benzylated amines.

Preferably, the molar reactant ratio of the benzaldehyde compound to the triaminononane is in a range from about 0.8:1 to about 3:1.

Preferably, wherein the molar reactant ratio of the benzaldehyde compound to the triaminononane is in a range from about 1.2:1 to about 2:1.

Preferably, the molar reactant ratio of the benzyl halide compound to the triaminononane is in a range from about 0.8:1 to about 3:1.

Preferably, wherein the molar reactant ratio of the benzyl halide compound to the triaminononane is in a range from about 1.2:1 to about 2:1.

Preferably, the curing agent composition has an amine hydrogen equivalent weight (AHEW) based on 100% solids from about 50 to about 250.

The present invention is also directed to a method for forming a curing agent composition comprising contacting a benzaldehyde compound or benzyl halide compound and a triaminononane compound under conditions sufficient to form at least one benzylated triaminononane compound.

Preferably, the at least one benzylated triaminononane compound has the following formula:

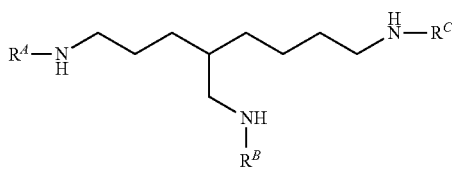

where $R^A$ is a substituted or unsubstituted benzyl group; $R^B$ and $R^C$ are independently $R^A$ or a hydrogen atom.

Preferably, the benzaldehyde compound and the triaminononane compound are reacted in a molar reactant ratio of the benzaldehyde compound to the triaminononane compound of about 0.8:1 to about 3:1.

Preferably, the benzaldehyde compound and the triaminononane compound are reacted in a molar reactant ratio of the benzaldehyde compound to the triaminononane compound of about 1.2:1 to about 2:1.

Preferably, the benzyl halide compound and the triaminononane compound are reacted in a molar reactant ratio of the benzyl halide compound to the triaminononane compound of about 0.8:1 to about 3:1.

Preferably, the benzyl halide compound and the triaminononane compound are reacted in a molar reactant ratio of the benzyl halide compound to the triaminononane compound of about 1.2:1 to about 2:1.

The present invention is also directed to an amine-epoxy composition comprising the contact product of: a curing agent composition comprising at least one benzylated triaminononane compound, the benzylated triaminononane compound being a reaction product of a benzaldehyde compound or benzyl halide compound and a triaminononane compound; and an epoxy composition comprising at least one multifunctional epoxy resin.

Preferably, the stoichiometric ratio of epoxy groups in the epoxy composition to amine hydrogens in the curing agent compositions is in the preferred range from about 1.5:1 to 0.5:1 and in particular 1.2:1 to about 0.7:1.

The present invention is also directed to an article comprising or manufactured using the amine-epoxy composition.

Preferably, the article is selected from the group consisting of adhesive, coating, primer, sealant, construction product, flooring product, and composite product.

In another embodiment, the benzylated triaminononane compound has the following formula:

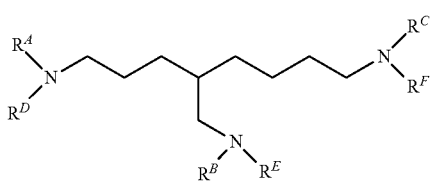

where $R^A$ is a substituted or unsubstituted benzyl group; $R^B$, $R^C$, $R^D$, $R^E$, and $R^F$ are independently $R^A$ or a hydrogen atom.

The present invention is also directed to a method for forming a curing agent composition comprising contacting a benzaldehyde compound or benzyl halide compound and a triaminononane compound under conditions sufficient to form at least one benzylated triaminononane compound, where the at least one benzylated triaminononane compound has the following formula:

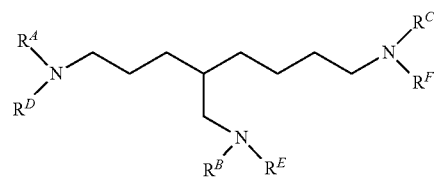

where $R^A$ is a substituted or unsubstituted benzyl group; $R^B$, $R^C$, $R^D$, $R^E$, and $R^F$ are independently $R^A$ or a hydrogen atom.

The present invention is also directed to a benzylated triaminononane compound comprising the reaction product of a benzaldehyde compound or benzyl halide compound and a triaminononane compound. Preferably, the benzylated triaminononane compound is a benzylated triaminononane.

Preferably, the benzylated triaminononane compound is a benzylated triaminononane of formula

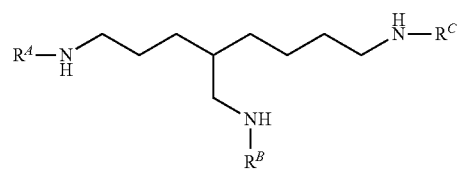

where $R^A$ is a substituted or unsubstituted benzyl group; $R^B$ and $R^C$ are independently $R^A$ or a hydrogen atom.

In another embodiment, the benzylated triaminononane compound is a benzylated triaminononane of formula

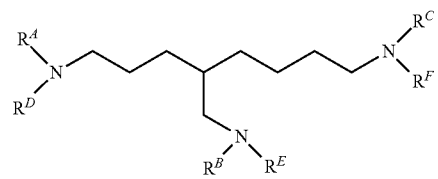

where $R^A$ is a substituted or unsubstituted benzyl group; $R^B$, $R^C$, $R^D$, $R^E$, and $R^F$ are independently $R^A$ or a hydrogen atom.

EXAMPLES

These Examples are provided to demonstrate certain aspects of the invention and shall not limit the scope of the claims appended hereto.

Example 1

This example describes the synthesis of Aminopropylated Ethylenediamine (APEDA).

The synthesis of aminopropylated ethylenediamine (APEDA) is a two step process. The first step involves the cyanoethylation of ethylenediamine (EDA) and the second step is the hydrogenation of cyanoethylated EDA to APEDA.

Step 1. EDA (1803 g) was charged to a 2 gal (7.56 L) reactor with 249.4 g of water. The reactor was filled with 50 psig (4.4 atm) nitrogen, stirred for 30 sec and depressurized. This process was repeated 3 times to remove all air from the reactor. After the final nitrogen purge, the reactor was filled with a nitrogen atmosphere and 3184 g of acrylonitrile was added using a high pressure liquid pump over 4 hr at 70° C. After the addition was complete the reactor temperature was maintained at 70° C. for an additional 30 min for the reaction to complete to afford di-cyanoethylated EDA.

Step 2: A 2 gal (7.56 L) Parr pressure reactor was charged with 785 g of isopropanol and 78 g of Raney Cobalt #2724 sponge metal catalyst. The reactor was sealed and pressure cycled 3 times with nitrogen to remove air and 3 times with hydrogen to remove the nitrogen. The vessel was then heated to 120° C. and pressurized to 800 psig (55.4 atm) with hydrogen. A total of 4200 g of di-cyanoethylated EDA from Step 1 was then added to the reactor in 4 hr at 120° C. using a high pressure liquid pump. The reactor contents were then kept for additional 90 min to complete the hydrogenation. After this 90 min post hydrogenation period the reactor was depressurized and the product was cooled down to 40° C. and filtered. This product was further processed in a rotary evaporator at 100-120° C. and 30-10 mm Hg to remove isopropanol, light components, and any residual water. The recovered product Am3-Am5 contained 2.3 wt % mono-aminopropylated EDA (Am3); 86.6% di-aminopropylated EDA (Am4); and 5.5 wt % tri-aminopropylated EDA (Am5). Table 1 also shows the viscosity, AHEW, amine values and pot life/gel time of the recovered product. The pot life/gel time was run on a 150 g mass comprising the amine curing agent composition mixed stoichiometrically with Epon 828 resin, a standard bisphenol-A based epoxy resin (DGEBA, EEW=190), and measured with a Techne gel timer at 25° C.

TABLE 1

| APEDA | |
|---|---|
| Example | 1 |
| Amine used | EDA |
| Amine ratio/CAN | 2/1 |
| Isopropanol (g) | 785 |
| Cyanoethylated Amine quantity (g) | 4200 |
| Raney Co #2724 catalyst (g) | 78 |
| % Di-aminopropylated amine | 86.6 |
| Viscosity at 25° C. (mPa · s) | 25.9 |
| AHEW | 29 |
| Amine Value (mg KOH/g) | 1273 |
| Gel time at 25° C. (min) | 39 |

Example 2

This example describes the synthesis of Benzylated APEDA (Am3-Am5) Mixture at a 1.2:1 Molar Ratio.

A 1 L Parr pressure reactor was charged with 435.8 g of APEDA mixture from Example 1 and 6.5 g of 5% palladium on carbon catalyst. The reactor was sealed and pressure cycled 3 times each with nitrogen to remove air and hydrogen to remove the nitrogen. The vessel was then depressurized and maintained under an atmosphere of hydrogen. A total of 344.8 g of benzaldehyde was then added to the reactor at a rate that took 10-20 min to complete using a high pressure metering pump. The temperature was stabilized at 80° C. and the hydrogen pressure was increased to 120 psig (9.2 atm) with hydrogen. These conditions were maintained for 75 min, when the temperature was then increased to 120° C. and the pressure to 800 psi (55.4 atm) for an additional 90 min.

The reactor was depressurized and the product was cooled down to 40° C. and filtered. This product was further processed in a rotary evaporator at 100-120° C. and 30-10 mm Hg to remove light components and any residual water.

The recovered product contained 53.4 wt % of mono-benzylated APEDA, 41 wt % di-benzylated APEDA and no detectable tri-benzylated APEDA.

Example 3

This example describes the synthesis of Benzylated APEDA Mixture at a 2.0:1 Molar Ratio.

The procedure of Example 2 was followed using 352.2 g of APEDA mixture from Example 1 and 5.3 g of 5% palladium on carbon catalyst and 424.5 g of benzaldehyde, except that after the benzaldehyde addition, the temperature was stabilized at 80° C. and the hydrogen pressure was increased to 120 psig (9.2 atm) with hydrogen and maintained at these conditions for 180 min.

The recovered product contained 9.7% of mono-benzylated APEDA and 85.2% di-benzylated APEDA and no detectable tri-benzylated APEDA. The gel times in Table 2 were determined following the procedure stated in Example 1.

TABLE 2

| Synthesis of Benzylated (Am3-Am5) APEDA | | |
|---|---|---|
| Example | 2 | 3 |
| Amine(s) used | Am3-Am5 | Am3-Am5 |
| Benzylating agent | Benzaldehyde | Benzaldehyde |
| Degree of benzylation | 1.2/1.0 | 2.0/1.0 |
| Amine quantity (g) | 484 | 352.2 |
| Benzylating agent (g) | 344.8 | 424.5 |
| Pd/C catalyst (g) | 6.5 | 5.3 |
| Free Amine by GC (%) | None detected | None detected |
| mono benzylated amines (%) | 53.4 | 9.7 |
| di benzylated amines (%) | 41 | 85.2 |
| tri benzylated amines (%) | None detected | None detected |
| Viscosity at 25° C. (mPa · s) | 68 | 123 |
| AHEW | 61 | 87.5 |
| Amine Value (mg KOH/g) | 764 | 641 |
| Gel time at 25° C. (min) | 83 | 100 |

Example 4

This example describes the synthesis of Benzylated Triaminononane 1.2/1.0 Molar Ratio.

The synthesis of benzylated triaminononane is a one-batch process. 372 g of triaminononane (2.15 mol) and 5.6 g of Pd/C catalyst were placed in a 1-liter autoclave batch reactor. The reactor was sealed and subsequently purged with nitrogen and then hydrogen to remove any air from the reactor. Over 10 minutes, 273.4 g of benzaldehyde (2.58 mol) were added to the reactor. After the addition of the benzaldehyde was complete, the reactor contents were stirred for an additional 5 minutes, at which time the reaction exotherm began to subside. At this point, the reactor was pressurized to 27.2 atm (400 psig) with hydrogen and the reactor was heated to 120° C. When the rate of hydrogen uptake slowed, the pressure was increased to 54.4 atm (800 psig). The hydrogenation process continued until the rate of hydrogen uptake fell below 0.0007 MPa/min (0.1 psi/min). The reactor was cooled to ambient temperature and depressurized, and the reaction product was filtered to remove the catalyst. Water was removed using a rotary evaporator operating under 40 mm Hg vacuum and temperatures up to 120° C. The resulting reaction product was benzylated triaminononane with viscosity, AHEW, and amine value measured. The properties are shown in Table 3. As shown in Table 3, no detectable amount of the tri benzylated product was observed.

Example 5

This example describes the synthesis of Benzylated Triaminononane 2.0/1.0 Molar Ratio.

The synthesis of benzylated triaminononane is a one-batch process. 232.5 g of triaminononane (1.34 mol) and 3.5 g of Pd/C catalyst were placed in a 1-liter autoclave batch reactor. The reactor was sealed and subsequently purged with nitrogen and then hydrogen to remove any air from the reactor. Over 10 minutes, 284.7 g of benzaldehyde (2.68 mol) were added to the reactor. After the addition of the benzaldehyde was complete, the reactor contents were stirred for an additional 5 minutes, at which time the reaction exotherm began to subside. At this point, the reactor was pressurized to 27.2 atm (400 psig) with hydrogen and the reactor was heated to 120° C. When the rate of hydrogen uptake slowed, the pressure was increased to 54.4 atm (800 psig). The hydrogenation process continued until the rate of hydrogen uptake fell below 0.0007 MPa/min (0.1 psi/min). The reactor was cooled to ambient temperature and depressurized, and the reaction product was filtered to remove the catalyst. Water was removed using a rotary evaporator operating under 40 mm Hg vacuum and temperatures up to 120° C. The resulting reaction product was benzylated triaminononane with viscosity, AHEW, and amine value measured. The properties are shown in Table 3.

Example 6

This example describes the synthesis of Benzylated Triaminononane 3.0/1.0 Molar Ratio.

The synthesis of benzylated triaminononane is a one-batch process. 232.5 g of triaminononane (1.34 mol) and 3.5 g of Pd/C catalyst were placed in a 1-liter autoclave batch reactor. The reactor was sealed and subsequently purged with nitrogen and then hydrogen to remove any air from the reactor. Over 15 minutes, 427.1 g of benzaldehyde (4.02 mol) were added to the reactor. After the addition of the benzaldehyde was complete, the reactor contents were stirred for an additional 5 minutes, at which time the reaction exotherm began to subside. At this point, the reactor was pressurized to 27.2 atm (400 psig) with hydrogen and the reactor was heated to 120° C. When the rate of hydrogen uptake slowed, the pressure was increased to 54.4 atm (800 psig). The hydrogenation process continued until the rate of hydrogen uptake fell below 0.0007 MPa/min (0.1 psi/min). The reactor was cooled to ambient temperature and depressurized, and the reaction product was filtered to remove the catalyst. Water was removed using a rotary evaporator operating under 40 mm Hg vacuum and temperatures up to 120° C. The resulting reaction was product was benzylated triaminononane with viscosity, AHEW, and amine value measured. The properties are shown in Table 3.

TABLE 3

Synthesis of Benzylated Triaminononane

| Example | 4 | 5 | 6 |
|---|---|---|---|
| Amine(s) used | Triaminononane | Triaminononane | Triaminononane |
| Benzylating agent | Benzaldehyde | Benzaldehyde | Benzaldehyde |
| Degree of benzylation | 1.2/1.0 | 2.0/1.0 | 3.0/1 |
| Amine quantity (g) | 372 | 232.5 | 232.5 |
| Benzylating agent (g) | 273.4 | 284.7 | 427.1 |
| Pd/C catalyst (g) | 5.6 | 3.5 | 3.5 |
| Free Amine by GC (%) | 7.8 | <0.1 | <0.1 |
| mono benzylated amines (%) | 45.6 | 12.1 | <0.1 |
| di benzylated amines (%) | 34.9 | 63.7 | 2.8 |
| tri benzylated amines (%) | 2.7 | 16.2 | 97.0 |
| Viscosity at 25° C. (mPa · s) | 47 | 100 | 173 |
| AHEW | 67 | 76 | 145 |
| Amine Value (mg KOH/g) | 597 | 476 | 379 |
| Gel time at 25° C. (min) | 80 | 118 | 449 |

Example 7

This example describes the synthesis of Benzylated Metaxylylenediamine 1.3/1.0 Molar Ratio.

The synthesis of benzylated metaxylylenediamine is a one-batch process. 645.8 g of m-xylylenediamine (4.74 mol) and 12.9 g of Pd/C catalyst were placed in a 2-liter autoclave batch reactor. The reactor was sealed and subsequently purged with nitrogen and then hydrogen to remove any air from the reactor. Over 20 minutes, 654.2 g of benzaldehyde (6.16 mol) were added to the reactor. After the addition of the benzaldehyde was complete, the reactor contents were stirred for an additional 5 minutes, at which time the reaction exotherm began to subside. At this point, the reactor was pressurized to 27.2 atm (400 psig) with hydrogen and the reactor was heated to 130° C. When the rate of hydrogen uptake slowed, the pressure was increased to 54.4 atm (800 psig). The hydrogenation process continued until the rate of hydrogen uptake fell below 0.0007 MPa/min (0.1 psi/min). The reactor was cooled to ambient temperature and depressurized, and the reaction product was filtered to remove the catalyst. Water was removed using a rotary evaporator operating under 40 mm Hg vacuum and temperatures up to 120° C. The resulting reaction product was benzylated m-xylylenediamine with viscosity, AHEW, and amine value measured. The properties are shown in Table 4.

TABLE 4

Synthesis of Benzylated Metaxylylenediamine

| Example | 7 |
|---|---|
| Amine(s) used | MXDA |
| Benzylating agent | Benzaldehyde |
| Degree of benzylation | 1.3/1.0 |
| Amine quantity (g) | 645.8 |
| Benzylating agent (g) | 654.2 |
| Pd/C catalyst (g) | 12.9 |
| Free Amine by GC (%) | 3.1 |
| mono benzylated amines (%) | 44.6 |
| di benzylated amines (%) | 42.8 |
| tri benzylated amines (%) | None detected |
| Viscosity at 25° C. (mPa · s) | 44.5 |

TABLE 4-continued

Synthesis of Benzylated Metaxylylenediamine

| Example | 7 |
|---|---|
| AHEW | 118 |
| Amine Value (mg KOH/g) | 448 |
| Gel time at 25° C. (min) | 316 |

Examples 8-12

Table 5 summarizes the amine-epoxy compositions used in Examples 8, 9, 10, 11 and 12. For instance, the composition of Example 11 was 100 g of EPIKOTE™ 828 epoxy resin, and 40.0 g of the curing agent composition of Example 5. As indicated in Table 3, Example 5 was a curing agent composition comprising the reaction product of triaminononane with benzaldehyde followed by reductive hydrogenation. The curing agents and their respective quantities shown in Examples 8, 9, 10, 11 and 12 were used as per Tables 2, 3 and 4. Table 6 summarizes the carbamation resistance of the amine-epoxy compositions used in Examples 8, 9, 10, 11 and 12.

TABLE 5

|  | Example 8 | Example 9 | Example 10 | Example 11 | Example 12 |
|---|---|---|---|---|---|
| Curing agent example | Ex. 2 | Ex. 3 | Ex. 4 | Ex. 5 | Ex. 6 |
| Weight of Curing Agent (g) | 32.2 | 46.1 | 35.0 | 40.0 | 49.0 |
| Resin Weight (g) | 100 | 100 | 100 | 100 | 100 |
| TFST @ 25° C. Phase 3 [h] | 3.75 | 6.25 | 5.5 | 7.1 | 9.0 |
| TFST @ 5° C. Phase 3 [h] | 12.0 | 9.0 | 13.1 | 15.8 | 21.0 |
| Gloss at 60° @ 25° C. [7 d] | 174 | 178 | 76 | 162 | 152 |
| Gloss at 60° @ 5° C. [7 d] | Matt | Matt | 35 | 140 | 65 |

TABLE 6

|  | Example 7 | Example 8 | Example 9 | Example 10 | Example 11 |
|---|---|---|---|---|---|
| Curing agent example | Ex. 2 | Ex. 3 | Ex. 4 | Ex. 5 | Ex. 6 |
| Carbamation rating 25° C. [7 d] | Poor | Very Good | Very Good | Very Good | Very Good |
| Carbamation rating 5° C. [7 d] | Poor | Poor | Very Good | Very Good | Good |

Carbamation panels rated where poor=white surface, very good=no damage/very good appearance, and good=is good appearance with slight damage.

Drying times for the amine-epoxy compositions are summarized in Table 5. The drying time was determined at 25° C. and 65% relative humidity (RH) using a Beck-Koller recorder, in accordance with ASTM D5895. The procedure involved coating glass panels with the amine-epoxy compositions at approximately 6 mils wet film thickness. The selection of a coating composition with either a long or short drying time depends upon the requirements of the end-use application. Generally, the results in Table 5 indicated that the coatings of inventive Examples 8, 9, 10, 11 and 12 had various drying times depending on the degree of benzylation used.

Table 5 also lists the 60° gloss test results after 7 days, at 25° C. and 50% RH. Results shown are the average of 10 measurements. Coatings were applied to glass panels at a wet film thickness of about 8 mils and tested in accordance with ASTM D523. The gloss was measured at an angle of 60° using a Gardner gloss meter. Measurements were made with the glass panel placed on a black cardboard background. As shown in Table 5, Example 10 has a lower gloss than Example 8 and Example 12 due to the higher content in free amine. Similarly, Example 11 has a lower gloss than Example 9 due to the higher content in free amine.

Tables 5 and 6 show that the speed of cure using benzylated triaminononane is similar to using benzylated APEDA (TFST Phase 3 at 25° C. and 5° C.) but with significantly better carbamation, water spotting and low temperature appearance. Table 5 also shows that using benzylated triaminononane gives better cure speeds than benzylated MXDA. According to examples 8-11, using benzylated triaminononane has similar cure speed, better carbamation resistance and better water spotting than using benzylated APEDA. According to examples 10-12, using benzylated triaminononane has faster cure speed, similar carbamation resistance and similar water spotting than using benzylated MXDA.

The invention claimed is:

1. A curing agent composition comprising at least one benzylated triaminononane compound, wherein the benzylated triaminononane compound comprises the reaction product of a benzaldehyde compound or benzyl halide compound and a triaminononane compound.

2. The composition of claim 1, wherein the benzylated triaminononane compound has the following formula:

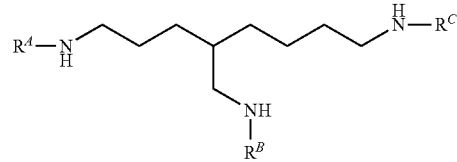

where $R^A$ is a substituted or unsubstituted benzyl group; $R^B$ and $R^C$ are independently $R^A$ or a hydrogen atom.

3. The composition of claim 2, wherein the composition comprises about 10-20% mono-benzylated amines, about 60-70% di-benzylated amines, and about 15-20% tri-benzylated amines.

4. The composition of claim 1, wherein the molar reactant ratio of the benzaldehyde compound to the triaminononane is in a range from about 0.8:1 to about 3:1.

5. The composition of claim 1, wherein the molar reactant ratio of the benzyl halide compound to the triaminononane is in a range from about 0.8:1 to about 3:1.

6. The composition of claim 1, wherein the curing agent composition has an amine hydrogen equivalent weight (AHEW) based on 100% solids from about 50 to about 250.

7. The composition of claim 1, wherein the benzylated triaminononane compound has the following formula:

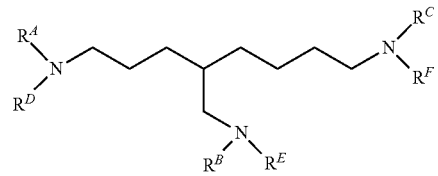

where $R^A$ is a substituted or unsubstituted benzyl group; $R^B$, $R^C$, $R^D$, $R^E$, and $R^F$ are independently $R^A$ or a hydrogen atom.

8. A method for forming a curing agent composition comprising contacting a benzaldehyde compound or benzyl halide compound and a triaminononane compound under conditions sufficient to form at least one benzylated triaminononane compound.

9. The method of claim 8, wherein the at least one benzylated triaminononane compound has the following formula:

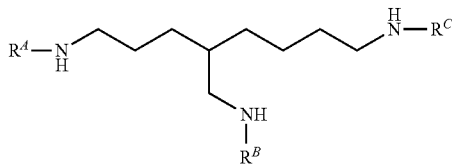

where $R^A$ is a substituted or unsubstituted benzyl group; $R^B$ and $R^C$ are independently $R^A$ or a hydrogen atom.

10. The method of claim 8, wherein the benzaldehyde compound and the triaminononane compound are reacted in a molar reactant ratio of the benzaldehyde compound to the triaminononane compound of about 0.8:1 to about 3:1.

11. The method of claim 8, wherein the benzyl halide and the triaminononane compound are reacted in a molar reactant ratio of the benzyl halide compound to the triaminononane compound of about 0.8:1 to about 3:1.

12. The method of claim 8, wherein the at least one benzylated triaminononane compound has the following formula:

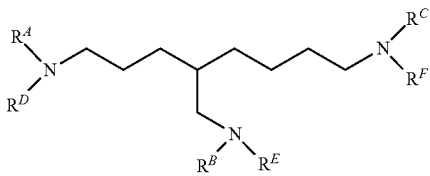

where $R^A$ is a substituted or unsubstituted benzyl group; $R^B$, $R^C$, $R^D$, $R^E$, and $R^F$ are independently $R^A$ or a hydrogen atom.

13. An amine-epoxy composition comprising the contact product of: a curing agent composition comprising at least one benzylated triaminononane compound, the benzylated triaminononane compound being a reaction product of a benzaldehyde compound or benzyl halide compound and a triaminononane compound; and an epoxy composition comprising at least one multifunctional epoxy resin.

14. The composition of claim 13 wherein the stoichiometric ratio of epoxy groups in the epoxy composition to amine hydrogens in the curing agent compositions is in the range from about 1.5:1 to 0.5:1.

15. The composition of claim 13 wherein the stoichiometric ratio of epoxy groups in the epoxy composition to amine hydrogens in the curing agent compositions is in the range from about 1.2:1 to about 0.7:1.

16. An article comprising the amine-epoxy composition of claim 13.

17. The article of claim 16, wherein the article is selected from the group consisting of adhesive, coating, primer, sealant, construction product, flooring product, and composite product.

18. A benzylated triaminononane compound comprising the reaction product of a benzaldehyde compound or benzyl halide compound and a triaminononane compound.

19. The benzylated triaminononane compound of claim 18, wherein the compound has the following formula:

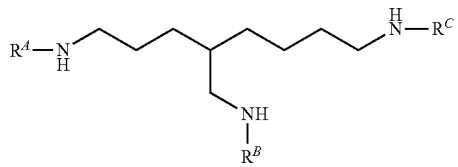

where $R^A$ is a substituted or unsubstituted benzyl group; $R^B$ and $R^C$ are independently $R^A$ or a hydrogen atom.

20. The benzylated triaminononane compound of claim 18, wherein the compound has the following formula:

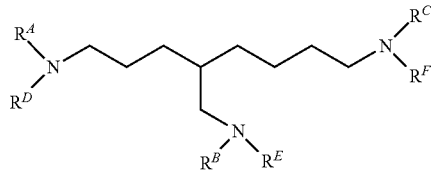

where $R^A$ is a substituted or unsubstituted benzyl group; $R^B$, $R^C$, $R^D$, $R^E$, and $R^F$ are independently $R^A$ or a hydrogen atom.

* * * * *